(12) United States Patent
Montia et al.

(10) Patent No.: US 11,000,635 B2
(45) Date of Patent: May 11, 2021

(54) ANTIMICROBIAL COMPOSITIONS COMPRISING MINOCYCLINE AND OXIDIZED CELLULOSE

(71) Applicants: Omrix Biopharmaceuticals Ltd., Rehovot (IL); Ethicon, Inc., Somerville, NJ (US)

(72) Inventors: Eve Montia, Rehovot (IL); Dwayne Looney, Flemington, NJ (US); Theresa Scheuble, Rockaway, NJ (US); Ronen Eavri, Binyamina (IL); Roi Mashiach, Rehovot (IL)

(73) Assignees: Omrix Biopharmaceuticals Ltd., Rehovot (IL); Ethicon, Inc., Somerville, NJ (US)

( * ) Notice: Subject to any disclaimer, the term of this patent is extended or adjusted under 35 U.S.C. 154(b) by 0 days.

(21) Appl. No.: 16/195,895

(22) Filed: Nov. 20, 2018

(65) Prior Publication Data
US 2019/0184068 A1   Jun. 20, 2019

Related U.S. Application Data

(60) Provisional application No. 62/598,662, filed on Dec. 14, 2017.

(30) Foreign Application Priority Data

Dec. 14, 2017  (IL) ........................................ 256312

(51) Int. Cl.
| | |
|---|---|
| *A61L 31/16* | (2006.01) |
| *A61K 31/717* | (2006.01) |
| *A61P 31/04* | (2006.01) |
| *A61L 15/28* | (2006.01) |
| *A61L 15/44* | (2006.01) |
| *A61L 26/00* | (2006.01) |
| *A61K 31/65* | (2006.01) |

(52) U.S. Cl.
CPC ............. *A61L 31/16* (2013.01); *A61K 31/65* (2013.01); *A61K 31/717* (2013.01); *A61L 15/28* (2013.01); *A61L 15/44* (2013.01); *A61L 26/0023* (2013.01); *A61P 31/04* (2018.01); *A61L 26/0066* (2013.01); *A61L 2300/404* (2013.01)

(58) Field of Classification Search
CPC .......... A61L 31/16; A61L 15/28; A61L 15/44; A61L 26/002; A61P 31/04; A61K 31/65; A61K 31/717
See application file for complete search history.

(56) References Cited

U.S. PATENT DOCUMENTS

| | | | | |
|---|---|---|---|---|
| 6,913,764 | B2 * | 7/2005 | Vogt | A61K 9/0024 |
| | | | | 424/423 |
| 8,646,456 | B2 | 2/2014 | Touati | |
| 9,095,603 | B2 * | 8/2015 | Shoseyov | A61K 31/716 |
| 9,533,069 | B2 | 1/2017 | Larsen | |
| 9,585,988 | B2 * | 3/2017 | McJames | A61L 31/08 |
| 9,675,728 | B2 * | 6/2017 | Cullen | A61L 15/44 |
| 10,420,864 | B2 * | 9/2019 | Pulapura | A61K 31/496 |
| 2009/0246287 | A1 * | 10/2009 | Shoseyov | A61K 31/716 |
| | | | | 424/499 |
| 2012/0185004 | A1 * | 7/2012 | McJames | A61L 31/10 |
| | | | | 607/3 |
| 2014/0031912 | A1 | 1/2014 | McJames | |
| 2016/0030476 | A1 | 2/2016 | Vachon | |
| 2017/0319754 | A1 * | 11/2017 | Pulapura | A61K 31/65 |
| 2018/0325740 | A1 * | 11/2018 | Kenny | A61K 31/717 |
| 2019/0046547 | A1 * | 2/2019 | Aslam | A61K 47/38 |
| 2019/0125938 | A1 * | 5/2019 | Chen | A61L 31/06 |
| 2019/0314560 | A1 * | 10/2019 | Soskin | A61K 31/496 |

FOREIGN PATENT DOCUMENTS

EP   1263485 B1   3/2005

OTHER PUBLICATIONS

Martina et al. Oxycellulose: Significant Characteristics in Relation to Its Pharmaceutical and Medical Applications. Advances in Polymer Technology, 2009, 28(3):199-208. (Year: 2009).*

S.K. Bajpai et al., "Minocycline-loaded cellulose nano whiskers/poly(sodium acrylate) composite hydrogel films as wound dressing", Int. J. Biol. Macro. 79 (2015): 76-85.

Clement L.K. Chia et al., "The Use of Collatamp G, Local Gentamicin-Collagen Sponge, in Reducing Wound Infection", Int. Surg. 2014 (99).

* cited by examiner

*Primary Examiner* — Robert A Wax
*Assistant Examiner* — Olga V. Tcherkasskaya
(74) *Attorney, Agent, or Firm* — David R. Crichton

(57) ABSTRACT

Disclosed are compositions comprised of Oxidized Cellulose (OC), such as oxidized regenerated cellulose (ORC), and an antibiotic comprised of minocycline, methods of preparation thereof and uses thereof.

7 Claims, 6 Drawing Sheets

ANTIMICROBIAL COMPOSITIONS COMPRISING MINOCYCLINE AND OXIDIZED CELLULOSE

FIELD OF THE INVENTION

The invention relates, inter alia, to the field of pharmaceuticals, and more specifically, but not exclusively, to an antimicrobial composition comprising oxidized cellulose (OC), such as oxidized regenerate[d] cellulose (ORC) and minocycline, methods of preparation thereof and uses thereof.

BACKGROUND OF THE INVENTION

Healthcare Associated Infections (HAIs) are infections which occur during treatment for medical or surgical conditions, and may be caused by surgical procedures or devices used in medical procedures, such as catheters or ventilators.

HAI are becoming a global epidemic, resulting in significant levels of morbidity and mortality, and involving significant health care costs. Health service providers, as well as bodies responsible for payment of associated costs, are focusing on reducing HAIs to improve outcomes and control costs.

Common types of HAIs include catheter-associated urinary tract infections, surgical site infections, bloodstream infections, pneumonia and *Clostridium difficile* infections.

Surgical Site Infections (SSI) are a class of HAI which develop following surgery. Types of SSI include superficial incisional SSI, which occurs in the area of the skin where the incision was made; deep incisional SSI, which occurs beneath the incision area in muscle and the tissue surrounding the muscles; and organ or space SSI, which can occur in any area of the body other than skin, muscle and surrounding tissue that was involved in the surgery, including a body organ or a space between organs.

SSIs are currently treated with systemic antibiotics, requiring high dosage levels, from which only a small percentage of the active substance reaches the target site. However, antimicrobial resistance among the pathogens causing the infection is becoming increasingly problematic, thereby limiting the usefulness of such antibiotics in the treatment or prevention of SSIs.

Known antibiotic-containing products include Medtronic Antibacterial Envelopes sold under the trademark TYRX™, comprising a combination of minocycline and rifampin, which have been shown to reduce infection associated with medical devices in multiple, randomized, controlled trials; the Codman® Bactiseal® catheter for drainage of external cerebrospinal fluid, which is impregnated with rifampin and clindamycin for reduction of Gram-positive bacteria on surfaces of the catheter tube; Ethicon plus sutures, a range of triclosan-coated sutures including a product sold under the trademark named MONOCRYL® Plus Antibacterial (poliglecaprone 25) Sutures and Plus Antibacterial (polydioxanone) Sutures sold under the trademark named PDS®; and CollatampG/Septocoll E—Inscroll/Biomet, a gentamicin-soaked Collagen Sponge Dual having a dual principle of action, for haemostasis and antibiotic protection.

Examples of background art include U.S. Publication No. 2014/0031912; In. Surg. 2014 (99): 565-570; EP 1263485B1; U.S. Pat. Nos. 9,533,069; 8,646,456; Int. J. Biol. Macro. 79 (2015): 76-85; and U.S. Publication No. 2016/0030476.

SUMMARY OF THE INVENTION

The invention, in some embodiments thereof, relates to a composition comprising Oxidized cellulose (OC), such as oxidized regenerated cellulose (ORC), and minocycline, methods of preparation thereof and uses thereof.

The present inventors have surprisingly found a synergistic effect between minocycline and OC such as ORC, such that significantly lower levels of minocycline than are generally known in the art when using minocycline alone can be used to obtain effective antimicrobial activity.

Specifically, in the composition of the present invention, minocycline may be present at a concentration of from about 2.7 µg to about 21.6 µg minocycline per 1.0 g ORC (equivalent to about 0.013 µg to about 0.105 µg/cm$^2$ ORC). This is significantly lower than the concentrations in the range of 0.6 µg to 5 µg minocycline per cm$^2$ which are known in the art, thereby resulting in less development of antibiotic resistance and fewer side effects, while providing broad spectrum antibiotic activity.

The composition, in some embodiments thereof, is suitable for local administration to subjects suffering from or at risk of an SSI, providing a higher level of antimicrobial activity than that of currently known compositions, such that lower amounts of antibiotics than are presently known in the art can be used.

As used herein, the term "antimicrobial" is intended to include destroying or inhibiting the growth of microorganisms such as pathogenic bacteria.

The term "antibiotic" as used herein relates to a substance such as a chemical that can destroy harmful bacteria or limit their growth. The substance can be a naturally produced or a synthetic material. In some embodiments, substance can be produced by a microorganism, or can be a semisynthetic substance derived from a microorganism.

As used herein, the term "minocycline" relates to a long-acting, broad-spectrum, antibiotic drug, $C_{23}H_{27}N_3O_7$, of CAS No. 10118-90-8, derived from tetracycline, or a pharmaceutically acceptable salt thereof. In some embodiments, minocycline is administered in the form of its hydrochloride $C_{23}H_{27}N_3O_7 \cdot HCl$ of CAS No. 13614-98-7.

The term "minocycline" as used herein, is intended to include, but not limited to, minocycline and pharmaceutically acceptable, pharmacologically active derivatives of minocycline, including both individual enantiomers of minocycline (dextrogyral and levogyral enantiomers) in their substantially pure form and their pharmaceutically acceptable salts, mixtures (in any ratio) of minocycline enantiomers and their pharmaceutically acceptable salts, and active metabolites of minocycline and their pharmaceutically acceptable salts.

The term "pharmaceutically acceptable salts" as used herein, includes salts which are suitable for use in contact with the tissues of humans without undue toxicity, irritation, allergic response and the like, which are well known in the art. Examples of pharmaceutically acceptable salts include, but are not limited to, any of the salts or co-crystals of minocycline selected from hydrochloride, hydrobromide, sulphate, citrate, phosphate, maleate, formate, acetate, nitrate, mesylate, succinate, benzoate and the like. The salts may be in the form of solvate, hydrate, hemihydrates, or anhydrous forms.

As used herein, the term "rifampin" relates to a naturally-occurring antibiotic, $C_{43}H_{58}N_4O_{12}$, of CAS No. 13292-46-1, produced by the soil bacterium *Amycolatopsis rifamycinica*, or a pharmaceutically acceptable salt thereof.

As used herein, the term "clindamycin", relates to a semi-synthetic antibiotic, $C_{18}H_{33}ClN_2O_5S$, of CAS No. 18323-44-9, derived from lincomycin, a natural antibiotic produced by the actinobacterium *Streptomyces lincolnensis*, or a pharmaceutically acceptable salt thereof. In some embodiments, clindamycin is administered in the form of its phosphate, $C_{18}H_{34}ClN_2O_8PS$, of CAS No. 24729-96-2 or hydrochloride, $C_{18}H_{34}Cl_2N_2O_5S$ of CAS No. 21462-39-5 or Hydrochloride Monohydrate of CAS Number 58207-19-5.

Aspects and embodiments of the invention are described in the specification hereinbelow and in the appended claims.

According to an aspect of some embodiments described herein, there is provided an antimicrobial composition comprising an oxidized cellulose (OC) such as oxidized regenerated cellulose (ORC), and minocycline, wherein the minocycline is present at a concentration of from about 2.7 µg to about 21.6 µg minocycline per 1.0 g ORC (equivalent to about 0.013 µg/cm² to about 0.105 µg/cm²), such as, for example, about 2.7 µg, about 3.0 µg, about 4.0 µg, about 5.0 µg, about 6.0 µg, about 7.0 µg, about 8.0 µg, about 9.0 µg, about 10.0 µg, about 11.0 µg, about 12.0 µg, about 13.0 µg, about 14.0 µg, about 15.0 µg, about 16.0 µg, about 17.0 µg, about 18.0 µg, about 19.0 µg, about 20.0 µg, about 21.0 µg or about 22.0 µg minocycline per 1.0 g ORC, including any value and range therebetween.

Accordingly, in some embodiments, there is provided an antimicrobial composition comprising an oxidized cellulose (OC), optionally, oxidized regenerated cellulose (ORC) and an antibiotic being minocycline, wherein the minocycline is present at a concentration of from about 2.7 µg to about 21.6 µg per 1.0 g OC.

According to some embodiments, minocycline is present in the antimicrobial composition at a concentration which is from about 2 to about 20 times lower than the Minimum inhibitory concentration (MIC) achieved in the absence of OC, i.e. minocycline is from about 2 to about 20 times more effective in the presence of the OC, for example, about 2 times, about 3 times, about 4 times, about 5 times, about 6 times, about 7 times, about 8 times, about 9 times, about 10 times, about 11 times, about 12 times, about 13 times, about 14 times, about 15 times, about 16 times, about 17 times, about 18 times, about 19 times or about 20 times more effective, including any value and range therebetween.

MIC relates herein to the lowest concentration of a chemical which prevents bacterial growth in a solution when the growth is monitored at an OD range of 595-600 nm e.g. as described in the "Examples" section. A MIC depends on the microorganism, the affected human being (in vivo only), and the antibiotic.

For example, the MIC of a chemical is determined by preparing solutions of the chemical in vitro at increasing concentrations, incubating the solutions with the separate batches of cultured bacteria, and monitoring the bacterial growth throughout time at the OD range of 595-600 nm. In order to define the MIC of a certain chemical the Effective Time 50 (ET50) is determined i.e. the time, in minutes, required for the antibiotic to induce a response halfway between the baseline and maximum OD reading at the range of 595-600 nm. The maximum OD is determined by bacterial growth in MHBII without the chemical. The first chemical concentration where the ET50 reached about ≥1650 minutes was determined as the MIC.

In some embodiments, the antimicrobial composition comprises ORC and minocycline, and is devoid of an additional antibiotic.

It has further been found that the synergistic effect of ORC and minocycline is not reduced upon addition of an additional antibiotic such as rifampin, clindamycin, or a mixture thereof, and in fact, the antimicrobial effect which occurs upon inclusion of such additional antibiotics in the compound was found to increase. Hence, according to some embodiments, the antimicrobial composition further comprises at least one additional antibiotic, such as, for example, rifampin, clindamycin or a combination thereof.

According to a further aspect of some embodiments described herein, there is provided an antimicrobial composition comprising an oxidized cellulose (OC), optionally oxidized regenerated cellulose (ORC), an antibiotic being minocycline, and at least one additional antibiotic, wherein the minocycline is present in the composition at a concentration of from about 0.5 µg to about 2.7 µg minocycline per 1.0 g ORC (equivalent to from about 0.013 to about 0.105 µg/cm²).

In some embodiments, "0.5 µg to about 2.7 µg minocycline" refers to about 0.5 µg, about 1.0 µg, about 1.1 µg, about 1.2 µg, about 1.3 µg, about 1.4 µg, about 1.5 µg, about 1.6 µg, about 1.7 µg, about 1.8 µg, about 1.9 µg, about 2 µg, about 2.1 µg, about 2.2 µg, about 2.3 µg, about 2.4 µg, about 2.5 µg, about 2.6 µg or about 2.7 µg minocycline per 1.0 g ORC, or, in some embodiments, about 6.0 ng/ml, about 6.25 ng/ml, about 6.3 ng/ml or about 6.5 ng/ml, including any value and range therebetween.

According to some embodiments, minocycline is present in the antimicrobial composition at a concentration which is from about 2 to about 200 times lower than that MIC achieved in the absence of OC and at least one additional antibiotic, i.e. minocycline is from about 2 to about 20 times more effective in the presence of the OC and the additional antibiotic, for example, about 2 times, about 5 times, about 10 times, about 20 times, about 30 times, about 40 times, about 50 times, about 60 times, about 70 times, about 80 times, about 90 times, about 100 times, about 110 times, about 120 times, about 130 times, about 140 times, about 150 times, about 160 times, about 170 times, about 180 times, about 190 times, or about 200 times more effective, including any value and range therebetween.

According to some embodiments, the antimicrobial composition further comprises at least one additional antibiotic.

Exemplary antibiotics include, but are not limited to, aminoglycosides, carbacephems, carbapenems, cephalosporins, cephamycins, penicillins, glycopeptides, quinolones, monobactams, macrolides, fluoroquinolones, and tetracyclines.

Further examples of antibiotics include, but are not limited to, Ampicillin; Amoxicillin; Aztreonam; Azlocillin; Azithromycin; Amikacin; Cephalothin; Cefaclor; Cefoxitin; Cefuroxime; Cefonicid; Cefmetazole; Cefotetan; Cefprozil; Cinoxacin; Cefetamet; Chloramphenicol; Clindamycin; Cefoperazone; Cefotaxime; Cloxacillin; Carbenicillin; Ciprofloxacin; Ceftizoxime; Ceftriaxone; Ceftazidime; Cefepime; Cephalexin; Cefixime; Co-amoxiclavuanate; Cefpodoxime; Cefsulodin; Clarithromycin; Dicloxacillin; Doxycycline; Erythromycin; Erythromycin estolate; Erythromycin ethyl succinate; Enoxacin; Erythromycin glucoheptonate; Erythromycin lactobionate; Erythromycin stearate; Fleroxacin; Gentamicin; Imipenem; Kanamycin; Lomefloxacin; Loracarbef; Methicillin; Nafcillin; Oxacillin; Mupirocin; Metronidazole; Mezlocillin; Nalidixic acid; Norfloxacin; Nitrofurantoin; Netilmicin; Ofloxacin; Penicillin G; Piperacillin; Rifampin; Streptomycin; Sulfamethoxazole; Tetracycline; Ticarcillin; Tobramycin; Teicoplanin; Trimethoprim; Vancomycin; Roxithromycin; combinations of Piperacillin and Tazobactam; and their various salts, acids, bases, and other derivatives.

In some embodiments, the at least one additional antibiotic is selected from the group consisting of rifampin, clindamycin and a combination thereof.

In some embodiments, the antimicrobial composition comprises ORC, minocycline and rifampin. In some embodiments, the antimicrobial composition comprises ORC, minocycline and clindamycin. In some embodiments, the antimicrobial composition comprises ORC, minocycline, rifampin and clindamycin.

In some embodiments, the at least one additional antibiotic comprises rifampin at a concentration of from about 31.4 µg to about 157 µg per 1.0 g OC.

In some embodiments, rifampin is present in the antimicrobial composition at a concentration of from about 30 µg to about 160 µg per 1.0 g ORC, such as, for example, about 34 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 105 µg, about 110 µg, about 115 µg, about 120 µg, about 125 µg, about 130 µg, about 135 µg, about 140 µg, about 145 µg, about 150 µg, about 155 µg or about 160 µg per 1.0 g ORC, including any value and range therebetween.

In some embodiments, the at least one additional antibiotic comprises clindamycin at a concentration of from about 0.6 µg to about 3.8 µg per 1.0 g OC.

In some embodiments, clindamycin is present in the composition at a concentration of from about 0.5 µg to about 4.0 µg per 1.0 g ORC, optionally from about 0.6 µg to about 3.8 µg per 1.0 g ORC, such as, for example, about 0.6 µg, about 0.8 µg, about 1.0 µg, about 1.2 µg, about 1.4 µg, about 1.6 µg, about 1.8 µg, about 2.0 µg, about 2.2 µg, about 2.4 µg, about 2.6 µg, about 2.8 µg, about 3.0 µg, about 3.2 µg, about 3.4 µg, about 3.6 µg or about 3.8 µg per 1.0 g ORC, including any value and range therebetween.

According to some embodiments, the composition further comprises an acid such as Trifluoroacetic acid (TFA).

According to some embodiments, the composition is provided in a solid form. In some such embodiments, the solid form is selected from the group consisting of a powder (compressed or non-compressed), a granule, and the like. In some such embodiments, the composition may be packaged for use in a solid form for application to a treatment site.

In some embodiments, the composition is provided in a form comprising a substrate comprising a pad, wherein the minocycline is dispersed or impregnated on and/or within the pad.

In some embodiments, the composition is provided in the form of a pad, wherein the minocycline is dispersed on and/or within the pad.

As used herein, the term "pad" relates to a piece of material used to protect a part of the body, give shape to something or clean something, and is intended to include a patch, a cloth, a mesh, a dressing, a fabric, a gauze, and the like.

As used herein, the term "patch" relates to a small piece of material that can be sewn or otherwise attached over a surface or wound.

As used herein, the term "cloth" relates to woven or felted fabric made from a fibre.

As used herein, the term "mesh" relates to a material made of a network of connected strands of flexible materials such as wire or thread.

As used herein, the term "dressing" relates to a covering for a wound.

As used herein, the term "fabric" relates to a flexible material consisting of a network of fibres produced by weaving, knitting, crocheting, knotting, felting or bonding.

As used herein, the term "gauze" relates to thin, loosely woven cloth used for dressings and swabs or to any material made of an open, mesh-like weave.

As used herein, the term "impregnate" means to saturate or infuse pores or spaces of a material, usually a solid material, with a substance, usually a liquid.

As used herein, the term "coating" relates to a covering layer applied to a surface of an object (usually referred to as a substrate), or to the process of applying such a covering layer.

As used herein, the term "substrate" relates to a material, such as a carrier, which provides the surface on which something is deposited.

As used herein, the term "solid" is intended to mean firm or stable in shape i.e. not liquid or fluid.

Bleeding is one of the risk factors contributing to increased SSI rate. To control blood loss at the surgical site, surgeons may use topical hemostats, such as ORC. In some embodiments of the present invention, the ORC is provided in the form of a hemostatic ORC pad, which is then impregnated with minocycline and optionally with one or more additional antibiotics, to provide a minocycline-impregnated ORC pad, which may be applied to the site of surgery, or inserted within the surgical cavity, wherein the one or more antibiotics are released from the antibiotic-impregnated ORC pad upon degradation of the ORC. This enables blood loss to be controlled during surgery while reducing or preventing bacterial infection related to the surgical procedure.

Hence, according to some embodiments, the composition is provided packaged for use in the form of a pad, such as a pad having a thickness of at least 200 µm. In some such embodiments, the thickness of the pad enables easy handling of the composition, for rapid and easy removal from the packaging and application to a treatment site.

According to some embodiments, the ORC pad is impregnated with minocycline as a single antibiotic or in combination with other antibiotics shown to be effective against a range of Gram-positive and Gram-negative organisms. In some such embodiments, a minocycline-impregnated ORC pad is applied to a surgical site prior to, during, or after closing of an incision. As the pad is absorbed by the body, sustained release of the minocycline and any additional antibiotics impregnated in the pad occurs directly at the surgical site, thereby helping to prevent local bacterial colonization that can lead to SSI.

According to a further aspect of some embodiments described herein, there is provided a method for the treatment of an infection in a subject in need thereof, the method comprising administering to the subject an antimicrobial composition comprising an oxidized cellulose (OC), optionally oxidized regenerated cellulose (ORC) and an antibiotic being minocycline, wherein the minocycline is present at a concentration of from about 2.7 µg to about 21.6 µg per 1.0 g OC (equivalent to from about 0.013 to about 0.105 µg/cm$^2$).

In some embodiments, "about 2.7 µg to about 21.6 µg per 1.0 g OC" refers to, for example, about 2.7 µg, about 3.0 µg, about 4.0 µg, about 5.0 µg, about 6.0 µg, about 7.0 µg, about 8.0 µg, about 9.0 µg, about 10.0 µg, about 11.0 µg, about 12.0 µg, about 13.0 µg, about 14.0 µg, about 15.0 µg, about 16.0 µg, about 17.0 µg, about 18.0 µg, about 19.0 µg, about 20.0 µg, about 21.0 µg or about 22.0 µg minocycline per 1.0 g ORC, including any value and range therebetween.

As used herein, the term "infection" relates to the invasion and multiplication of disease-causing microorganisms such as bacteria. An infection may cause no symptoms and be subclinical, or it may cause symptoms and be clinically apparent. An infection may remain localized, or it may spread through the blood or lymphatic vessels to become systemic (body wide). Microorganisms that live naturally in the body without resulting in disease are not considered infections. For example, certain bacteria that normally live within the mouth and intestine are not infections.

As used herein, the term "treatment" of an infection is intended to include curing, ameliorating, stabilizing or preventing the infection and/or symptoms thereof in a subject suffering from or at risk of the infection. As used herein, the term "ameliorating" an infection includes reducing the severity and/or duration of the infection and/or symptoms thereof.

In some embodiments of the method, treatment comprises preventing and/or ameliorating the infection and/or symptoms thereof.

In some embodiments of the method, the antimicrobial composition comprises ORC and minocycline, and is devoid of an additional antibiotic.

According to a further aspect of some embodiments described herein, there is provided a method for the treatment of an infection in a subject in need thereof, the method comprising administering to the subject an antimicrobial composition comprising an oxidized cellulose (OC) such as oxidized regenerated cellulose (ORC), an antibiotic being minocycline, and at least one additional antibiotic, wherein the minocycline is present at a concentration of from about 0.5 µg to about 2.7 µg per 1.0 g OC. In some embodiments of the method, the infection is an SSI.

In some embodiments, the minocycline is present at a concentration of about 0.5 µg, about 1.0 µg, about 1.1 µg, about 1.2 µg, about 1.3 µg, about 1.4 µg, about 1.5 µg, about 1.6 µg, about 1.7 µg, about 1.8 µg, about 1.9 µg, about 2 µg, about 2.1 µg, about 2.2 µg, about 2.3 µg, about 2.4 µg, about 2.5 µg, about 2.6 µg or about 2.7 µg minocycline per 1.0 g ORC, including any value and range therebetween.

In some such embodiments, the at least one additional antibiotic is selected from the group consisting of rifampin, clindamycin and a combination thereof.

In some embodiments of the method, the antimicrobial composition comprises ORC, minocycline and rifampin. In some embodiments, the antimicrobial composition comprises ORC, minocycline and clindamycin. In some embodiments, the antimicrobial composition comprises ORC, minocycline, rifampin and clindamycin.

In some embodiments of the method, rifampin is present in the antimicrobial composition at a concentration of from about 30 µg to about 160 µg per 1.0 g ORC. In some embodiments, rifampin is present in the antimicrobial composition at a concentration of, for example, about 34 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 105 µg, about 110 µg, about 115 µg, about 120 µg, about 125 µg, about 130 µg, about 135 µg, about 140 µg, about 145 µg, about 150 µg, about 155 µg or about 160 µg per 1.0 g ORC, including any value and range therebetween.

In some embodiments of the method, clindamycin is present in the composition at a concentration of from about 0.5 µg to about 4.0 µg per 1.0 g ORC.

In some embodiments of the method, clindamycin is present in the antimicrobial composition at a concentration of, for example, from about 0.6 µg to about 3.8 µg per 1.0 g ORC, such as, for example, about 0.6 µg, about 0.8 µg, about 1.0 µg, about 1.2 µg, about 1.4 µg, about 1.6 µg, about 1.8 µg, about 2.0 µg, about 2.2 µg, about 2.4 µg, about 2.6 µg, about 2.8 µg, about 3.0 µg, about 3.2 µg, about 3.4 µg, about 3.6 µg or about 3.8 µg per 1.0 g ORC, including any value and range therebetween.

As used herein, the term "oxidized cellulose (OC)" is meant to include materials/products/articles/compositions/formulations comprising or consisting essentially of OC, e.g. a dressing, fibrin glue, synthetic glue, pad, matrix, powder, tab, pill, suture, fiber, stent, implant, scaffold, solution, gel, wax, gelatin and the like.

In some embodiments of the method, the OC comprises or consists essentially of Oxidized Regenerated Cellulose (ORC).

According to some embodiments of the method, the composition is provided in a solid form.

In some embodiments of the method, the OC, such as ORC, is provided in the form of a powder (compressed or non-compressed), a bead, a granule, an aggregate, a fiber (including a woven, nonwoven, knitted, milled or fine fiber and combinations thereof), all either independently used or dispersed in a pharmaceutically acceptable vehicle or in other forms.

In some embodiments of the method, the OC, such as ORC, is provided in the form of a substrate comprising a pad, wherein the minocycline is dispersed on and/or within the pad. In some such embodiments, the substrate optionally further comprises an additional material together with the OC.

In some embodiments of the method, the OC is provided in the form of a pad, wherein the minocycline is dispersed on and/or within the pad.

In some embodiments of the method, the OC (e.g. ORC) is provided in the form of a dressing that utilizes a fabric as a substrate, where the fabric substrate comprises fibers prepared from a biocompatible polymer(s) and comprises a surface that possesses properties suitable for use as a hemostat, e.g. strength, flexibility and porosity.

In certain embodiments of the invention, the OC (e.g. ORC) may further include a hemostatic agent, or other biological or therapeutic compounds, moieties or species, including drugs and pharmaceutical agents.

In certain embodiments, the composition according to the invention includes OC (e.g. ORC) comprising a pad coated or impregnated with minocycline, and optionally including at least one additional coated or impregnated antibiotic.

An efficient concentration of minocycline coated or impregnated in the pad is about 2.7 µg to about 21.6 µg per 1.0 g ORC (equivalent to from about 0.013 µg/cm$^2$ to about 0.105 µg/cm$^2$), such as, for example, about 2.7 µg, about 3.0 µg, about 4.0 µg, about 5.0 µg, about 6.0 µg, about 7.0 µg, about 8.0 µg, about 9.0 µg, about 10.0 µg, about 11.0 µg, about 12.0 µg, about 13.0 µg, about 14.0 µg, about 15.0 µg, about 16.0 µg, about 17.0 µg, about 18.0 µg, about 19.0 µg, about 20.0 µg, about 21.0 µg or about 22.0 µg minocycline per 1.0 g ORC, including any value and range therebetween.

When the at least one additional coated or impregnated antibiotic is present, an effective concentration of minocycline can be from about 0.5 µg to about 2.7 µg per 1.0 g ORC, such as about 0.5 µg, about 1.0 µg, about 1.1 µg, about 1.2 µg, about 1.3 µg, about 1.4 µg, about 1.5 µg, about 1.6 µg, about 1.7 µg, about 1.8 µg, about 1.9 µg, about 2 µg, about 2.1 µg, about 2.2 µg, about 2.3 µg, about 2.4 µg, about 2.5 µg, about 2.6 µg or about 2.7 µg minocycline per 1.0 g ORC, including any value and range therebetween.

Non-limiting examples of commercially available dressings comprising OC that can be used according to the invention include products sold under the trademarks: INTERCEED®, EVARREST®, SURGICEL®, SURGICEL NU-KNIT®, SURGICEL FIBRILLAR®, SURGICEL SNOW®, and OXYCEL®.

In one embodiment, the OC (e.g. ORC) is included within a device/article and/or as a coating on a device/article; such as implant, pacemaker, drain, artificial knee, etc.

As used herein, the term "fiber" relates to a structure having an elongated threadlike form. In some embodiments, a fiber has an aspect ratio (i.e. the ratio of length to thickness) of at least about 3:1.

In one embodiment, the fibers have a size distribution of D90 of less than 350 μm, and D50 of less than 167 μm.

In some embodiments, the composition of the invention also comprises fibers of size 350 μm.

Size distribution D50 is also known as the median diameter or the medium value of the units in the powder/aggregates size distribution, it is the value of the units' diameter at 50% in the cumulative distribution. For example, if D50 is X μm, then 50% of the units in the sample are larger than X μm, and 50% are smaller than X μm. Size distribution is the number of units that fall into each of the various size ranges given as a percentage of the total number of all units' sizes in the sample of interest. Accordingly, D90 value refers to 90% of the units having a size that is smaller than the D90 value. All ranges disclosed herein include the upper and lower limit, where applicable.

In one embodiment, OC (such as ORC) fibers have a size distribution of D90 of less than 177 μm and D50 of less than 95 μm.

As used herein, the term "powder" relates to dry, solid, loose particles of small grain size.

As used herein, the term "aggregate" relates to a compressed material.

According to a further aspect of some embodiments described herein, there is provided a kit comprising an oxidized cellulose (OC) optionally oxidized regenerated cellulose (ORC) and an antibiotic being minocycline.

According to a further aspect of some embodiments described herein, there is provided a kit comprising an oxidized cellulose (OC) optionally oxidized regenerated cellulose (ORC) and an antibiotic being minocycline, wherein the minocycline is present at a concentration of from about 2.7 μg to about 21.6 μg minocycline per 1.0 g OC.

In some embodiments of the kit, the antimicrobial composition comprises ORC and minocycline, and is devoid of an additional antibiotic.

In some embodiments of the kit, the antimicrobial composition comprises minocycline impregnated in the ORC.

According to a further aspect of some embodiments described herein, there is provided a method for the preparation of an antimicrobial composition, the method comprising combining an oxidized cellulose (OC) such as oxidized regenerated cellulose (ORC) and an antibiotic being minocycline, wherein the minocycline is present at a concentration of from about 2.7 μg to about 21.6 μg per 1.0 g OC.

In some embodiments of the method, the antimicrobial composition comprises ORC and minocycline, and is devoid of an additional antibiotic.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced.

In the Figures:

In FIGS. 1-6: The x-axis refers to time (min), and the y-axis refers to optical density (OD) at 600 nm.

FIG. 2 presents line graphs showing the effect of addition of ORC on the antibiotic activity of rifampin at various concentrations of the rifampin: 0.25 μg/ml (upper left panel), 0.125 μg/ml (upper middle panel), 0.062 μg/ml (upper right panel), 0.015 μg/ml (lower left panel), 0.031 μg/ml (lower middle panel), and 0 μg/ml (PBS control; lower right panel).

FIG. 3 presents line graphs showing the effect of addition of ORC on the antibiotic activity of clindamycin at various concentrations of the clindamycin: 0.25 μg/ml (upper left panel), 0.125 μg/ml (upper middle panel), 0.065 μg/ml (upper right panel), 0.032 μg/ml (lower left panel), and 0 μg/ml (PBS control; lower right panel).

FIG. 4 presents line graphs showing the effect of addition of ORC on the antibiotic activity of gentamycin at various concentrations of the gentamycin: 1 μg/ml (upper left panel), 0.8 μg/ml (upper middle panel), 0.5 μg/ml (upper right panel), 0.3 μg/ml (lower left panel), 0.1 μg/ml (lower middle panel), and 0 μg/ml (PBS control; lower right panel).

FIG. 5 presents line graphs showing the effect of addition of ORC on the antibiotic activity of tetracycline, at various concentrations of the tetracycline: 0.4 μg/ml (upper left panel), 0.2 μg/ml (upper middle panel), 0.1 μg/ml (upper right panel), 0.05 μg/ml (lower left panel), 0.025 μg/ml (lower middle panel), and 0 μg/ml (PBS control; lower right panel).

FIG. 6 presents line graphs summarizing the antibiotic effect of ORC alone (Blank ORC; upper right panel) or ORC together with antibiotics as in FIGS. 1 to 5: gentamycin (upper left panel), tetracycline (upper middle panel), rifampin (lower left panel), clindamycin (lower middle panel) and minocycline (lower right panel).

DESCRIPTION OF SOME EMBODIMENTS OF THE INVENTION

Figure 1:
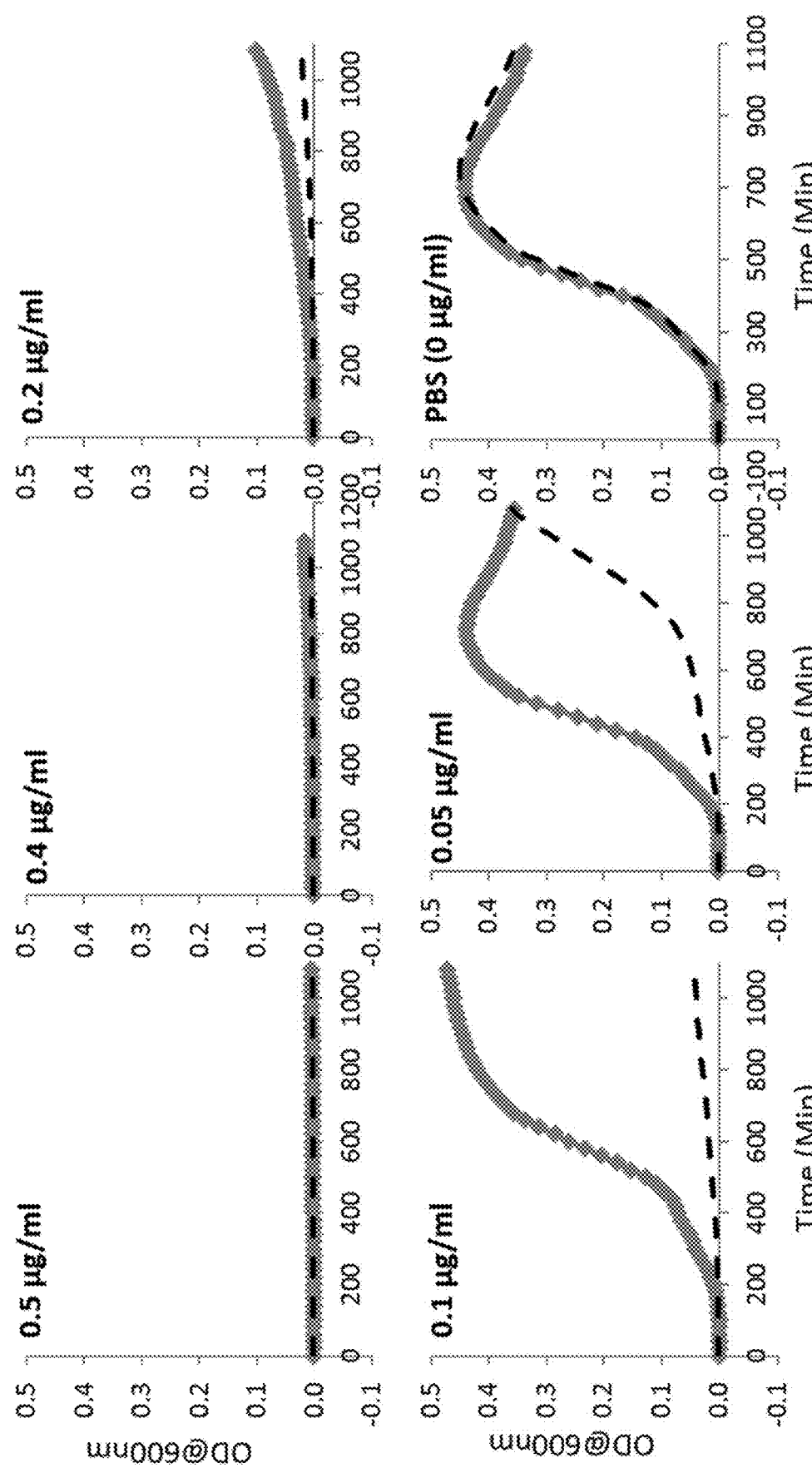
FIG. 1 presents line graphs showing the effect of addition of oxidized regenerated cellulose (ORC) on the antibiotic activity of minocycline at various concentrations of the minocycline: 0.5 μg/ml (upper left panel), 0.4 μg/ml (upper middle panel), 0.2 μg/ml (upper right panel), 0.1 μg/ml (lower left panel), 0.05 μg/ml (lower middle panel), and 0 μg/ml (PBS control; lower right panel); PBS: phosphate-buffered saline.

The invention, in some embodiments thereof, relates to a composition comprising a cellulose-based material such as oxidized regenerated cellulose (ORC) and minocycline, methods of preparation thereof and uses thereof.

The principles, uses and implementations of the teachings herein may be better understood with reference to the accompanying description. Upon perusal of the description, one skilled in the art is able to implement the invention without undue effort or experimentation.

Before explaining at least one embodiment in detail, it is to be understood that the invention is not necessarily limited in its application to the details of construction and the arrangement of the components and/or methods set forth in the following description. The invention is capable of other embodiments or of being practiced or carried out in various ways. The phraseology and terminology employed herein are for descriptive purpose and should not be regarded as limiting.

As shown in the Examples below, the present inventors conducted as a primary stage a preliminary minimal inhibitory concentration (MIC) test for minocycline, in order to confirm the antibiotic effect of minocycline on the bacterial strains tested. Serial dilutions of the antibiotic were prepared and the MIC was determined as the dilution at which visible growth of bacteria was first seen. The minocycline MIC for S. aureus was found to be 0.25 µg/ml, which is consistent with the minocycline MIC values reported in the literature (0.06-0.5 µg/ml).

Following establishment of the MIC, the present inventors studied the interaction between ORC and minocycline by incubating the minocycline at a concentration equal to or lower than the MIC, in the presence or absence of ORC pads. Upon addition of a small amount of ORC to the growth medium, the antimicrobial activity of minocycline was significantly enhanced, resulting in an MIC of 0.05 µg/ml that is about five times that of the MIC without the ORC.

The levels of ORC studied in combination with the minocycline were carefully chosen to be below their intrinsic antimicrobial activity in order to ensure that antimicrobial activity obtained with the combination could not be attributed to the effect of ORC alone or to an additive effect of ORC with minocycline. For this purpose, pads of dimensions approximately 1×1.5 inch, weighing between 65-75 mg (70 mg on average) were used.

In addition, any acidifying effect of the ORC was buffered, such as by adding a buffering agent to the composition, thereby forming an isotonic non-acidic medium for the bacteria to grow in.

When antibiotics other than minocycline were tested in combination with ORC, no enhancement of antibiotic activity was seen. In fact, some tested antibiotics (such as gentamycin and rifampin) showed a reduction in the antibiotic activity as compared to the antibiotic alone, indicating interference between the ORC and antibiotic.

The synergistic effect between minocycline and ORC persisted when additional antibiotics (rifampin and/or clindamycin), which did not themselves exhibit a synergistic effect with ORC, were added to the mixture of minocycline and ORC. Moreover, the additional of such additional antibiotics resulted in a further increase of antibiotic activity, in addition to that seen with minocycline and ORC. Use of such combinations of antibiotics provides a wide coverage of Gram negative and Gram positive antibiotics.

Minocycline-impregnated ORC pads were then prepared by immersing ORC pads in solutions of minocycline dissolved in methanol, followed by drying, in order to determine the best minocycline concentrations to be used for a minocycline-ORC product.

MIC of 0.0126 µg/ml was obtained in the presence of ORC, as compared to 0.25 µg/ml in the absence of ORC (Table 1), the MIC being at least 5.8-fold lower in the presence of ORC than that in its absence. The MIC of minocycline together with ORC, when ORC was impregnated with minocycline was 12.60 ng/ml, the MIC being at least 19.8-fold lower in the presence of ORC than that in its absence. The MIC of minocycline with ORC, when ORC was impregnated with minocycline and the at least one more antibiotic was 200-fold lower of the MIC for minocycline alone. For example, 1.26 ng/ml minocycline in combination with 38.96 ng/ml clindamycin (total 10.22 ng/ml antibiotic loaded) together with ORC (from antibiotic-impregnated ORC) is a sufficient level of antibiotic to provide a high level of antibiotic activity.

EXAMPLES

The present inventors aimed to identify a preferred antibiotic for impregnation into an ORC pad. A study was conducted in 3 stages as described below.

Materials and Methods

Materials

Tryptic Soy broth (TSB) was acquired from Hy-Labs, Rehovot, Israel (Cat #BP266/1009).

Mueller Hinton Broth II (MHBII) was acquired from Becton Dickinson, New Jersey, USA (Catalog no. (Cat #) BBL298268).

Staphylococcus aureus (S. aureus), Strain #6538 was acquired from ATCC.

ORC pads used were Surgicel® from Ethicon, Cat #1951.

Phosphate buffer Saline (PBS) was acquired from Biological Industries Ltd., Beit Haemek, Israel (Cat #20-023-1A).

0.8/0.2 µm syringe filters were acquired from Pall Corporation, New York, USA (Cat #: 4658).

Antibiotics were acquired from Tokyo Chemical Industry (TCI), Tokyo, Japan as follows: Minocycline (Cat #: M2288); Gentamycin (Cat #: G0383); Rifampin (Cat #: R0079); Clindamycin (Cat #: C2256); and Tetracycline (Cat #: T2525).

Sterile water (SW) used was milli-Q purified water subjected to sterilization using a 0.2-micron cellulose acetate filter.

Orbital shaker: Thermo Fisher sold under the trademark MaxQ™ 4450 Benchtop Orbital Shakers.

Methods

Preparation of Inoculum

An isolated colony of S. aureus bacteria was picked from afresh streak plate (no more than 1 week old). The colony was transferred into 3-4 ml of TSB and incubated overnight in an orbital shaker at 35° C.-37° C.

The following day, the turbidity of the actively-growing broth culture was adjusted with Calcium-adjusted Mueller Hinton broth II (MHBII) to be equivalent to that of a 0.5 McFarland standard ($1\times10^8$ CFU/ml). The broth culture was maintained under ambient conditions prior to use.

No more than 15 minutes prior to use, the culture was further diluted 20 fold in MHBII to obtain a final $5\times10^6$ CFU/ml stock suspension.

Preparation of ORC Extracts

ORC pads undergo hydrolyzation, resulting in degradation, when immersed in an aqueous solution, such that resulting ORC particles interfere with OD readings and provide inaccurate results. In order to avoid this, extracts from the ORC pads were obtained as described below and used in the present study.

a. Preparation of Blank ORC Extracts

ORC pads which had not been impregnated with antibiotic (referred to herein as "blank ORC pads") were subjected to extraction in PBS for three hours at ambient temperature. Extract obtained from these blank ORC pads is referred to herein as "blank ORC extract".

b. Preparation of Blank ORC Extracted in Antibiotic

Blank ORC pads i.e. ORC pads which had not been impregnated with antibiotic (referred to herein as "blank ORC pads"), were subjected to extraction in a solution of antibiotic in PBS for three hours at ambient temperature.

Extract obtained from blank ORC pads in a solution of antibiotic in PBS is referred to herein as "blank ORC extracted in antibiotic".

Due to the acidity of ORC, which provides some antibiotic effect, the size of the pad used was small i.e. approximately 1×1.5 inch, weighing between 65-75 mg (70 mg on average) in order to prevent the ORC from affecting the final pH of the assay and therefore the growth of the bacteria.

15 ml tubes, each containing 3 ml of an antibiotic solution at a known concentration in sterile PBS, were prepared in duplicate.

Blank ORC pads were subjected to extraction in the antibiotic solution by immersing the ORC pads in the antibiotic solution for 3-5 hours at ambient temperature on a roller mixer (Stuart, Cat #SRT9D).

The extraction fluid was filtered using 0.8/0.2 µm syringe filters (Pall, Cat #4658) and mixed with calcium-adjusted MHBII to provide antibiotic-ORC test suspension.

c. Preparation of Antibiotic-Impregnated ORC Extract

Solutions comprising different concentrations of antibiotics to be tested were prepared in methanol.

Blank ORC pads of dimensions 1×1.5 inch, weighing between 65-75 mg (70 mg on average), in duplicate, were immersed in the antibiotic solutions and then dried using a rotary evaporator to provide "antibiotic-impregnated ORC pads".

15 ml test tubes containing 3 ml of sterile PBS were prepared, and the antibiotic-impregnated ORC pads were immersed in the tubes and incubated for 3-5 hours at ambient temperature on a roller mixer (Stuart, Cat #SRT9D).

Each of the above extracts was filtered out using a sterile 0.8/0.2 µm syringe filter into a clean 15 ml tube. These extraction fluids are referred to herein as "antibiotic-impregnated ORC extracts".

Example 1: Primary Stage Determination of Antibiotic MIC

The purpose of this stage was to confirm antibiotic activity according to MIC levels reported in the literature, to establish specific activity for the antibiotic, and to identify the preferred antibiotic for further studies.

Antibiotics tested were minocycline, rifampin, clindamycin, gentamycin and tetracycline.

MIC Measurement

The method used in this stage was based on the classic Minimum Inhibitory Concentration (MIC) measurements, as described by the Clinical and Laboratory Standards Institute (CLSI) document M07-A9: "Method for Dilution Antimicrobial Susceptibility Test for Bacteria that Grow Aerobically". While classic MIC measurements require visual inspection of plates for bacterial growth after 18 hours, growth was monitored in the present study according to optical density (OD) at 600 nm, using an ELISA reader (MultiSkan™ FC ELISA reader, Thermo Fisher Scientific, Massachusetts, USA), thereby obtaining bacterial growth curves for tested antibiotic solutions.

A 96-well assay plate layout (Corning Cat #3596) was prepared as follows:

Columns 1 and 3-12: 100 µl of MHBII alone was added to each well.

Row 2: 200 µl of a solution of antibiotic in MHBII at the highest concentration to be tested was added to each well.

A series of 2-fold dilutions was performed, wherein 100 µl of solution of antibiotic was withdrawn from each well of column 2, transferred to the corresponding well of column 3, and mixed.

The dilution was then repeated by transfer from column 3 to column 4, and so on, until column 11, when the 100 µl of solution of antibiotic withdrawn from each well of column 11 was discarded.

The 5×10$^6$ CFU/ml stock suspension which had been prepared in advance was transferred into a reservoir and 10 µl of the stock suspension were added into each well of columns 2-11 using a multichannel pipette to obtain a final 5×105 CFU/ml suspension.

The plate was then incubated at 37° C. with shaking in the ELISA reader and the optical density at 600 nm was read every 20 minutes for a total of 18 hours.

The average OD reading obtained for each antibiotic concentration was calculated and plotted against time to obtain a growth curve.

The MIC was determined as the first antibiotic concentration at which some bacterial growth occurred by the end of the 18-hour period.

Results

Results are presented in Table 1 below.

TABLE 1

| Antibiotic Conc. | MIC values for S. aureus according to CLSI (µg/ml) | MIC values for S. aureus found in the present study (µg/ml) |
|---|---|---|
| Rifampin | 0.004-0.015 | 0.015 |
| Clindamycin | 0.06-0.25 | 0.062 |
| Minocycline | 0.06-0.5 | 0.25 |
| Gentamicin | 0.12-1 | 0.25 |
| Tetracycline | 0.06-0.5 | 0.06 |

As seen in Table 1, the MIC values obtained in the present study were consistent with those published e.g. by the CLSI.

Example 2: Secondary Stage Determination of Interaction of Antibiotics with OC This stage comprised MIC measurements for several antibiotics, either alone or in combination with ORC pads, in order to identify any interference of enhancement of the antibiotic activity in the presence of ORC.

MIC Measurement

The preferred antibiotic concentrations, as established in the first stage, were used for antibiotics in combination with the ORC pads.

The various antibiotics tested and the concentrations used are shown in Table 2 below.

TABLE 2

| Antibiotic | Conc. 1 (µg/ml) | Conc. 2 (µg/ml) | Conc. 3 (µg/ml) | Conc. 4 (µg/ml) | Conc. 5 (µg/ml) | MIC determined in Example 1 (µg/ml) |
|---|---|---|---|---|---|---|
| Minocycline | 0.5 | 0.4 | 0.2 | 0.1 | 0.05 | 0.25 |
| Rifampin | 0.11 | 0.055 | 0.028 | 0.014 | 0.007 | 0.015 |
| Clindamycin | 0.25 | 0.125 | 0.062 | 0.031 | N/A | 0.062 |
| Gentamicin | 1 | 0.8 | 0.5 | 0.3 | 0.1 | 0.25 |
| Tetracycline | 0.4 | 0.2 | 0.1 | 0.05 | 0.025 | 0.06 |

Blank ORC extracted in antibiotic and blank ORC extracts, prepared as described above, were diluted 10 folds in MHBII in sterile 15 ml capped tubes.

The 5×10$^6$ CFU/ml stock suspension which had been prepared in advance was transferred into a reservoir and 10 µl of the stock suspension were added into each well of columns 2-11 using a multichannel pipette to obtain a final 5×105 CFU/ml suspension.

The plate layout used is shown in Table 3 below.

TABLE 3

| | 1 | 2 | 3 | 4 | 5 | 6 | 7 | 8 | 9 | 10 | 11 | 12 |
|---|---|---|---|---|---|---|---|---|---|---|---|---|
| A | SW | SW | SW | SW | SW | SW | SW | SW | SW | SW | SW | SW |
| B | SW | BLANK | Ab Conc. 1 + ORC | Ab Conc. 1 + ORC | Ab Conc. 1 + ORC | Ab Conc. 1 + ORC | Ab Conc. 1 | Ab Conc. 1 | Ab Conc. 1 | Ab Conc. 1 | W/O | SW |
| C | SW | BLANK | Ab Conc. 2 + ORC | Ab Conc. 2 + ORC | Ab Conc. 2 + ORC | Ab Conc. 2 + ORC | Ab Conc. 2 | Ab Conc. 2 | Ab Conc. 2 | Ab Conc. 2 | W/O | SW |
| D | SW | BLANK | Ab Conc. 3 + ORC | Ab Conc. 3 + ORC | Ab Conc. 3 + ORC | Ab Conc. 3 + ORC | Ab Conc. 3 | Ab Conc. 3 | Ab Conc. 3 | Ab Conc. 3 | W/O | SW |
| E | SW | BLANK | Ab Conc. 4 + ORC | Ab Conc. 4 + ORC | Ab Conc. 4 + ORC | Ab Conc. 4 + ORC | Ab Conc. 4 | Ab Conc. 4 | Ab Conc. 4 | Ab Conc. 4 | W/O | SW |
| F | SW | +ve Ctrl. | Ab Conc. 5 + ORC | Ab Conc. 5 + ORC | Ab Conc. 5 + ORC | Ab Conc. 5 + ORC | Ab Conc. 5 | Ab Conc. 5 | Ab Conc. 5 | Ab Conc. 5 | +ve Ctrl. | SW |
| G | SW | +ve Ctrl. | PBS-ORC | PBS-ORC | PBS-ORC | PBS-ORC | PBS | PBS | PBS | PBS | +ve Ctrl. | SW |
| H | SW | SW | SW | SW | SW | SW | SW | SW | SW | SW | SW | SW |

150 μl sterile water (SW) was added to each of the border wells (i.e. columns 1 and 12, rows A and H) in order to prevent any drying effect for the duration of the experiment.

Column 2, rows B to E were left as blanks, i.e. containing no antibiotics without bacteria, in order to provide a reference for the basic OD of the plate.

Columns 3 to 6, rows B to F, were filled with the Blank ORC extracted in antibiotic at decreasing concentrations 1 to 5, diluted 10 folds in MHBII. Each sample tested was placed in 4 well repeats for statistical results.

Columns 7 to 10, rows B to F, were filled with the antibiotic solution (AB) at decreasing concentrations 1 to 5, diluted 10 folds in MHBII. Each sample tested was placed in 4 well repeats for statistical results.

Columns 2 and 11, rows F and G, contained as a positive control (+ve) antibiotic alone, at low and high concentrations, prepared from a stock solution of the test antibiotic in PBS, diluted in sterile MHBII.

Columns 3 to 6, row G, were filled with Blank-ORC extract (PBS-ORC) diluted 10 folds in MHBII. These samples were used as a negative control in order to ascertain that the bacteria were not significantly affected by the ORC alone and that any bacterial growth impairment detected was due to the effect of the antibiotic.

Columns 7 to 10, row G, were filled with PBS alone (PBS), diluted 10-fold in MHBII, as a further negative control.

Column 11, rows B to E, contained a further negative control comprising MHBII alone bacteria and no antibiotic (MHBII) providing the bacterial growth performance in these conditions without any antibacterial interference (W/O).

At least 4 wells contained bacteria alone in MHBII in order to verify that no interference in bacterial growth occurred.

The plate was incubated at 37° C. with shaking in the ELISA reader and the optical density at 600 nm was read every 20 minutes for a total of 18 hours.

The average and standard deviation for OD readings was calculated for each time point of the wells using Excel. The average values were plotted against time to obtain a graph of the bacterial growth curves in the presence of each of the antibiotics tested.

In some cases, the average OD was plotted for a single endpoint of 800 minutes for the various antibiotic treatments and controls. The endpoint of 800 minutes was selected as this was found to be the time at which the difference between the various antibiotic concentrations is the greatest.

The average values were also entered into the GraphPad Prism program (GraphPad Software Inc., CA, USA) in order to calculate the Effective Time 50 (ET50) i.e. the time, in minutes, required for the antibiotic to induce a response halfway between the baseline and maximum, where the maximum is the bacterial growth in MHBII with PBS. This provides a quantifiable measure of the efficacy of the antibiotics tested and enables comparison of the various samples tested. It is noted that ET50 values of above 1650 are indicative of high antibiotic activity while ET50 values of greater than 2000 minutes were found to be imprecise and are therefore regarded as maximal growth inhibition. The range of 1000 to 1650 is indicative of positive antibiotic activity. In cases, wherein there was such limited growth that an ET50 value could not be established, the result is indicated as N/A.

In order to compare different antibiotic concentrations, the average OD at 800 minutes for each sample tested was plotted against the antibiotic concentration and the EC50 calculated i.e. the concentration of antibiotic which induces a response halfway between the baseline and maximum after a specified exposure time.

Results a. Minocycline

Results are shown in Table 4 below and in FIG. 1.

TABLE 4

| | Minocycline concentration | | | | | | | | | | | |
|---|---|---|---|---|---|---|---|---|---|---|---|---|
| | 0 µg/ml | | 0.05 µg/ml | | 0.1 µg/ml | | 0.2 µg/ml | | 0.4 µg/ml | | 0.5 µg/ml | |
| | −ORC | +ORC | −ORC | +ORC | −ORC | +ORC | −ORC | +ORC | −ORC | +ORC | −ORC | +ORC |
| ET50 | 411.7 | 423.6 | 428.1 | 901.1 | 555.1 | >2000 | 1771 | >2000 | >2000 | >2000 | >2000 | >2000 |

The results show that addition of ORC to minocycline resulted in a strong synergistic effect. The effect was greater at lower concentrations of minocycline, where the antibiotic activity of minocycline alone was low.

For example, 0.05 µg/ml minocycline alone had no antibiotic effect alone (ET50 428.1 minutes, which is very similar to the ET50 value of 411.7 minutes obtained in the absence of minocycline). Following addition of ORC to the minocycline solution, the ET50 was increased to 901 minutes.

A similar effect was seen with minocycline concentrations of 0.1 µg/ml of (ET50 of 555 and over 2000 in the absence and presence, respectively, of ORC) and 0.2 µg/ml (ET50 of 1771 and over 2000 in the absence and presence, respectively, of ORC).

Since 0.4 µg/ml of minocycline alone showed an ET50 of above 2000 minutes, such that maximal growth inhibition was shown, the addition of ORC to the antibiotic solution did not produce any increase in antibiotic effect.

ORC alone, in the amount used, did not show any antibiotic effect.

b. Rifampicin (Rifampin)

Figure 2:
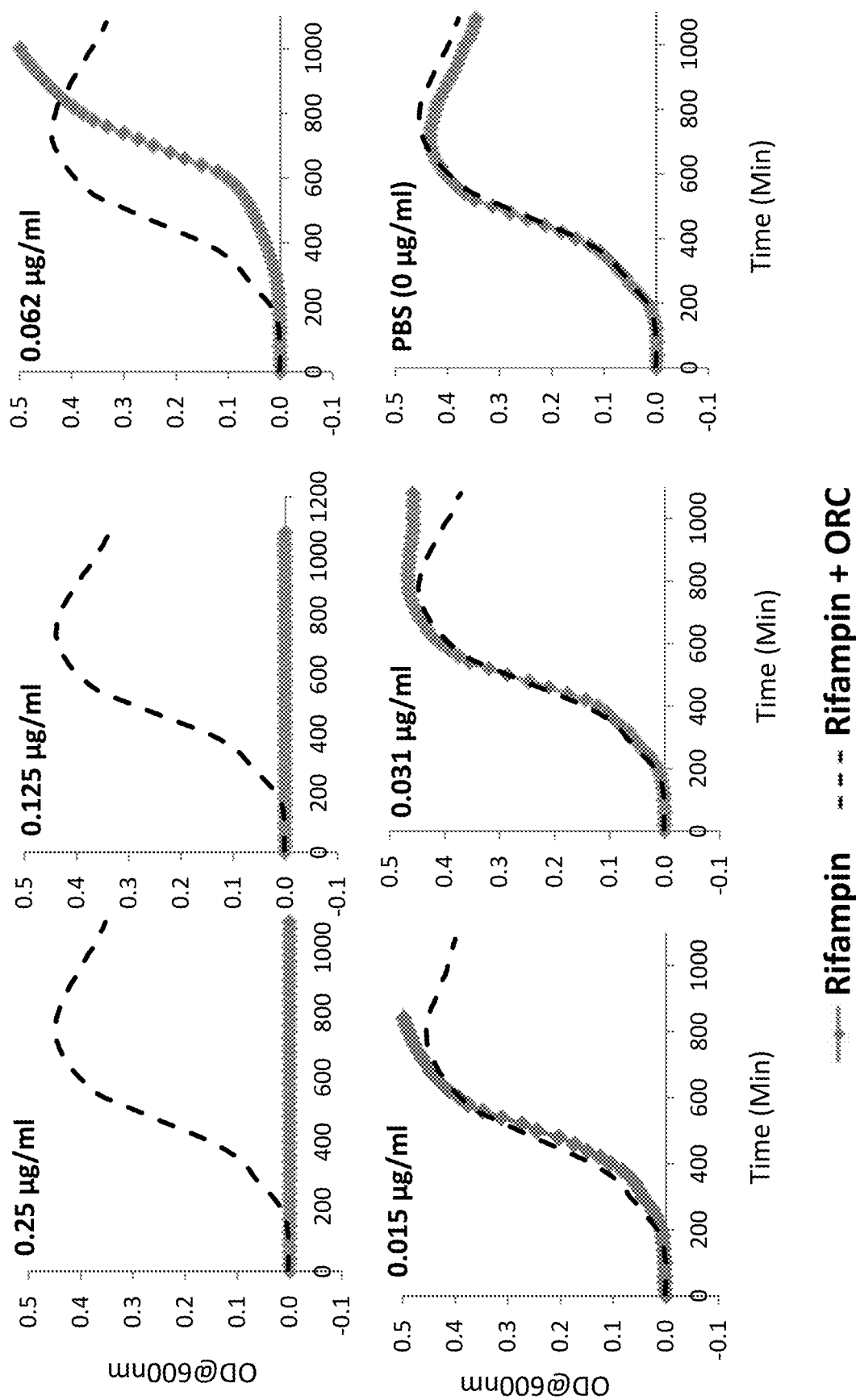

Results are shown in Table 5 below and in FIG. 2.

TABLE 5

| | Rifampin Concentration | | | | | | | | | | | |
|---|---|---|---|---|---|---|---|---|---|---|---|---|
| | 0 µg/ml | | 0.015 µg/ml | | 0.031 µg/ml | | 0.062 µg/ml | | 0.125 µg/ml | | 0.25 µg/ml | |
| | −ORC | +ORC | −ORC | +ORC | −ORC | +ORC | −ORC | +ORC | −ORC | +ORC | −ORC | +ORC |
| ET50 | 424.9 | 432.8 | 470.7 | 440.5 | 448.4 | 436.3 | 669.1 | 432.8 | N/A | 432.3 | N/A | 430.8 |

The results show that ORC interferes with the antibiotic activity of rifampin, such that no antibiotic activity was seen upon addition of ORC to solutions of rifampin at concentrations which showed antibiotic activity when used alone.

For example, at concentrations of 0.25 µg/ml and 0.125 µg/ml rifampin alone there was no growth at all (no ET50 values were therefore available). However, once ORC was added to the rifampin solutions, the growth profile resembled that of the control (ET50 values of around 430 minutes). At a concentration of 0.062 µg/ml rifampin, delayed bacterial growth was seen (ET50 of 669.1), but the antibiotic activity was decreased by the addition of ORC, reducing the ET50 value to 430 minutes.

c. Clindamycin

Figure 3:
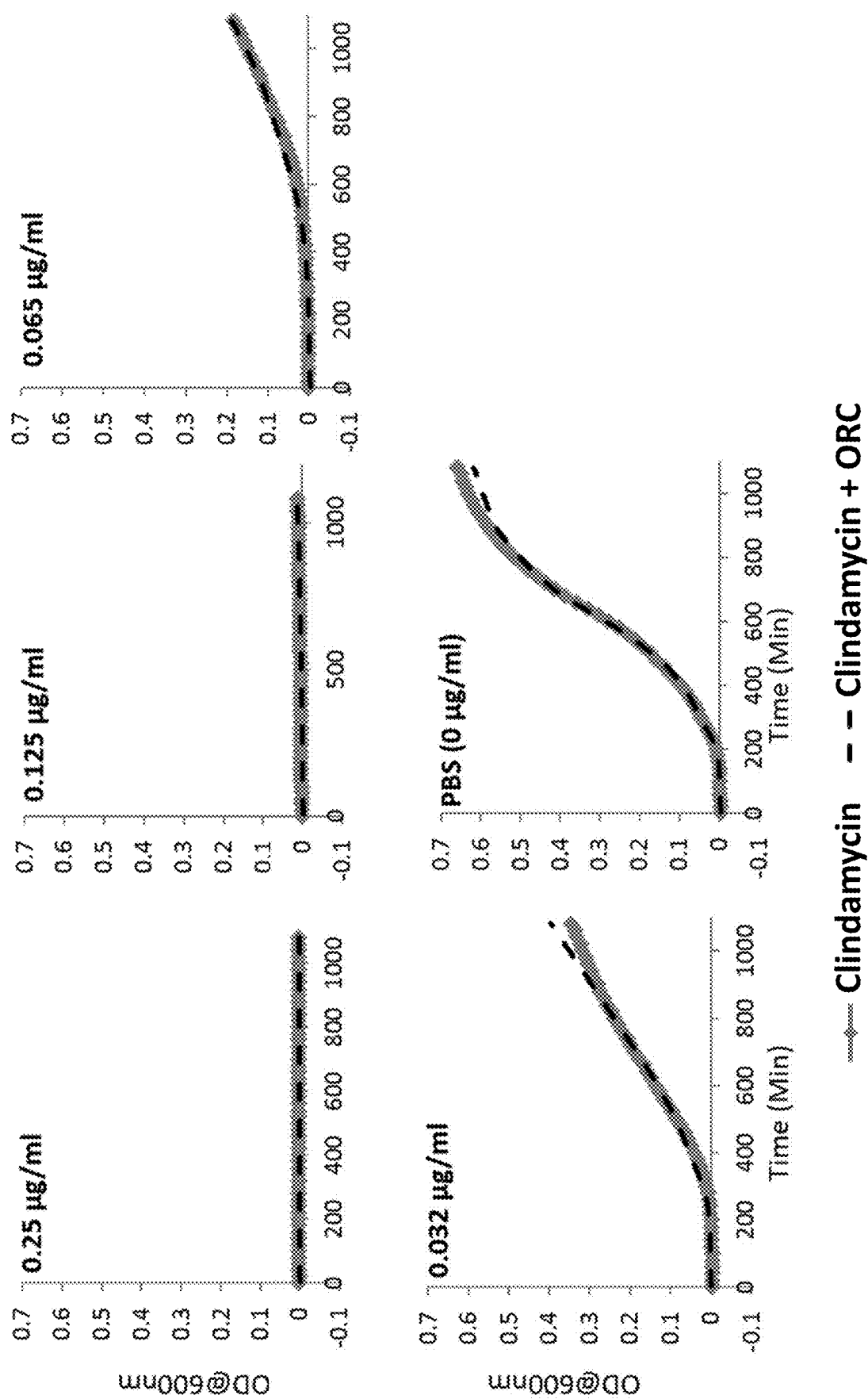

Results are shown in Table 6 below and in FIG. 3.

TABLE 6

| | Clindamycin concentration | | | | | | | | | |
|---|---|---|---|---|---|---|---|---|---|---|
| | 0 µg/ml | | 0.03125 µg/ml | | 0.0625 µg/ml | | 0.125 µg/ml | | 0.25 µg/ml | |
| | −ORC | +ORC | −ORC | +ORC | −ORC | +ORC | −ORC | +ORC | −ORC | +ORC |
| ET50 | 650.2 | 648 | 1001 | 1049 | 1494 | 1432 | >2000 | >2000 | N/A | N/A |

The results show that addition of ORC had no effect on the antibiotic activity of clindamycin at the clindamycin concentrations tested.

d. Gentamycin

Figure 4:
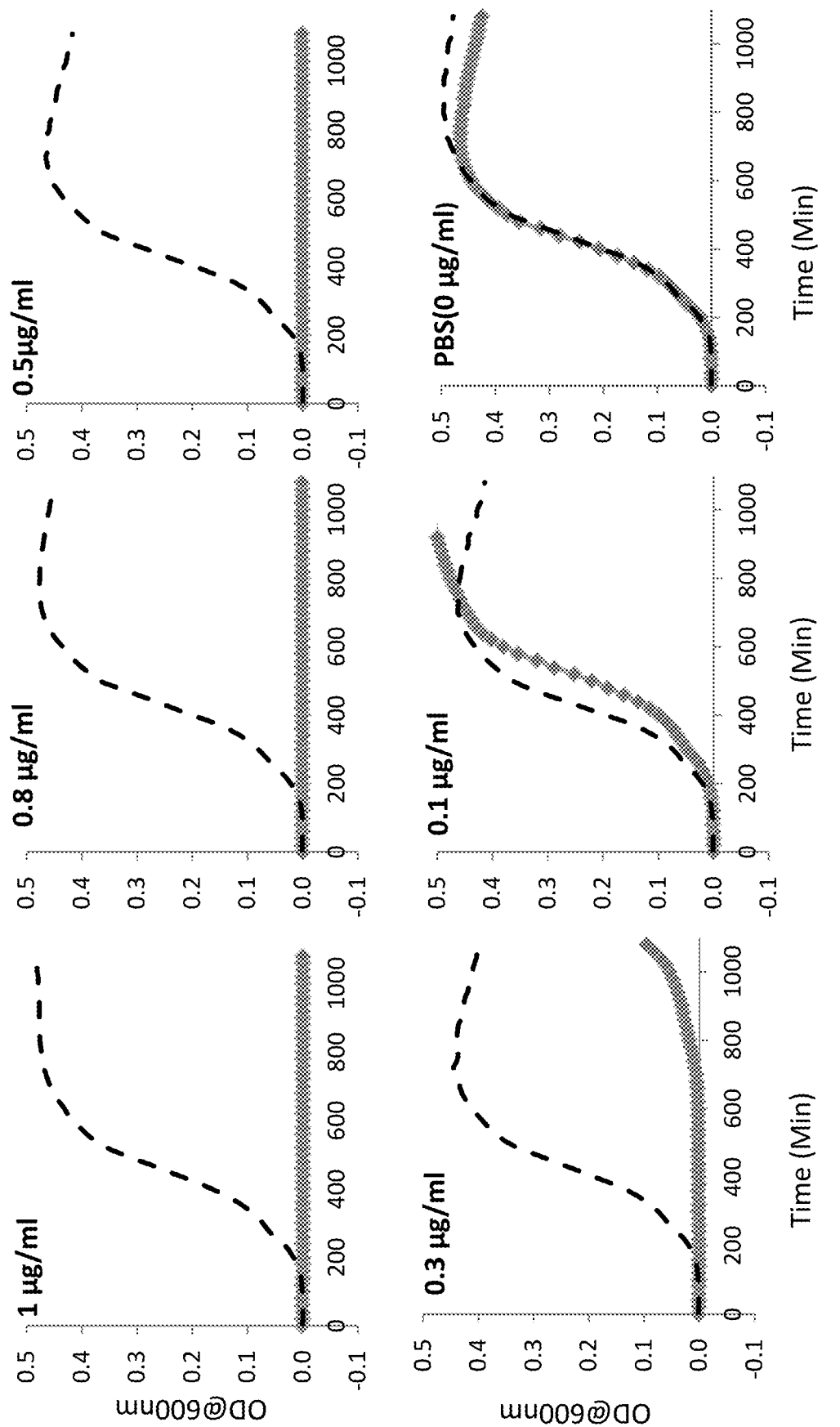

Results are shown in Table 7 below and in FIG. 4.

TABLE 7

| | Gentamycin Conc. | | | | | | | | | | | |
|---|---|---|---|---|---|---|---|---|---|---|---|---|
| | 0 µg/ml | | 0.1 µg/ml | | 0.3 µg/ml | | 0.5 µg/ml | | 0.8 µg/ml | | 1 µg/ml | |
| | −ORC | +ORC | −ORC | +ORC | −ORC | +ORC | −ORC | +ORC | −ORC | +ORC | −ORC | +ORC |
| ET50 | 414.1 | 420.7 | 509.4 | 423.7 | 1360 | 429.3 | N/A | 423.1 | N/A | 422.7 | N/A | 446.6 |

The results show that addition of ORC to solutions of gentamycin resulted in decreased antibiotic activity at all gentamycin concentrations tested.

e. Tetracycline

Figure 5:
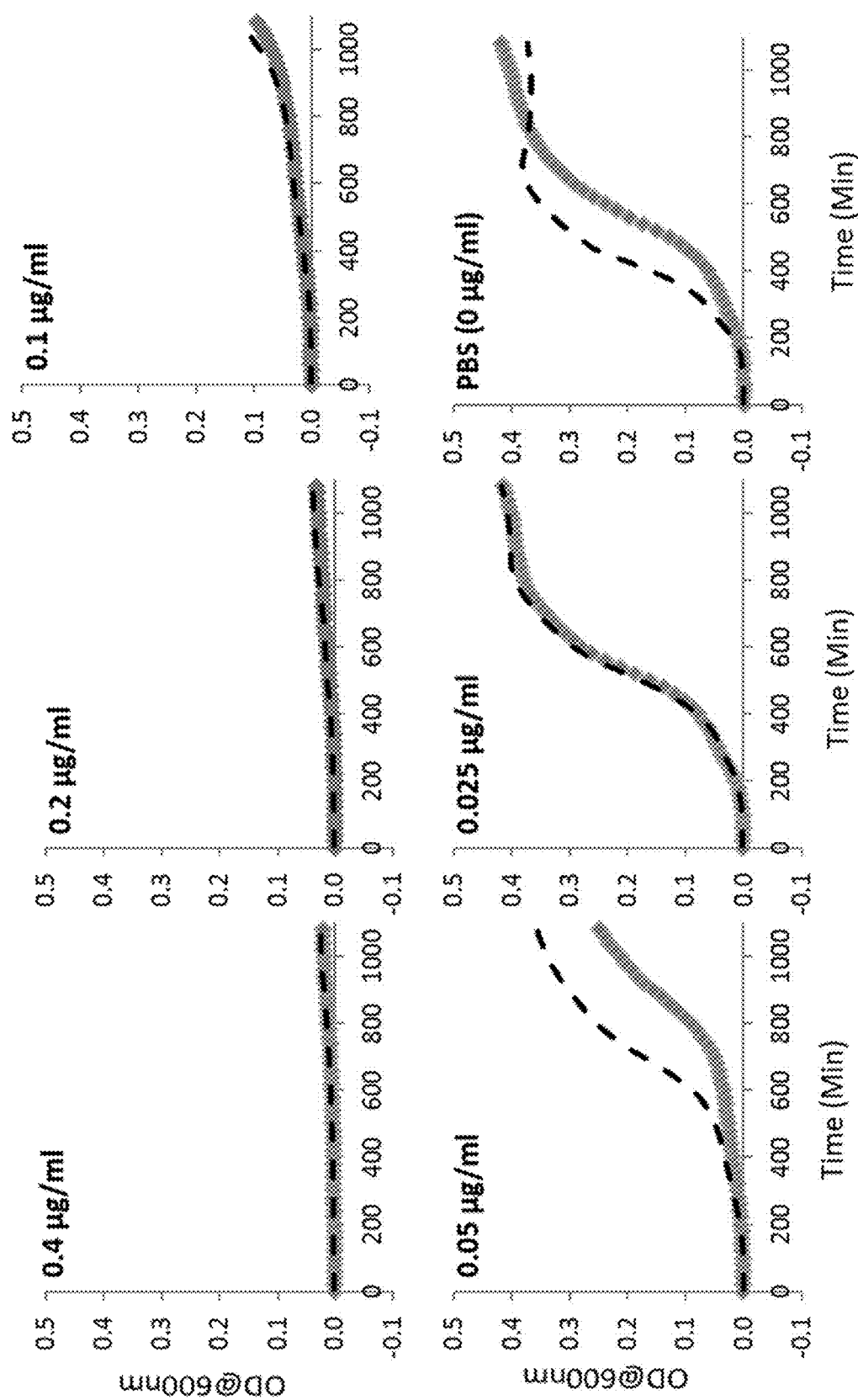

Results are shown in Table 8 below and in FIG. 5.

TABLE 8

| | Tetracycline Conc. | | | | | | | | | | | |
|---|---|---|---|---|---|---|---|---|---|---|---|---|
| | 0 µg/ml | | 0.025 µg/ml | | 0.05 µg/ml | | 0.1 µg/ml | | 0.2 µg/ml | | 0.4 µg/ml | |
| | −ORC | +ORC | −ORC | +ORC | −ORC | +ORC | −ORC | +ORC | −ORC | +ORC | −ORC | +ORC |
| ET50 | 565.6 | 425.3 | 531.1 | 517.7 | 989.9 | 741.1 | 1889 | 1470 | >2000 | >2000 | >2000 | >2000 |

The results show that addition of ORC had no effect on the antibiotic activity of tetracycline at the tetracycline concentrations tested.

Figure 6:
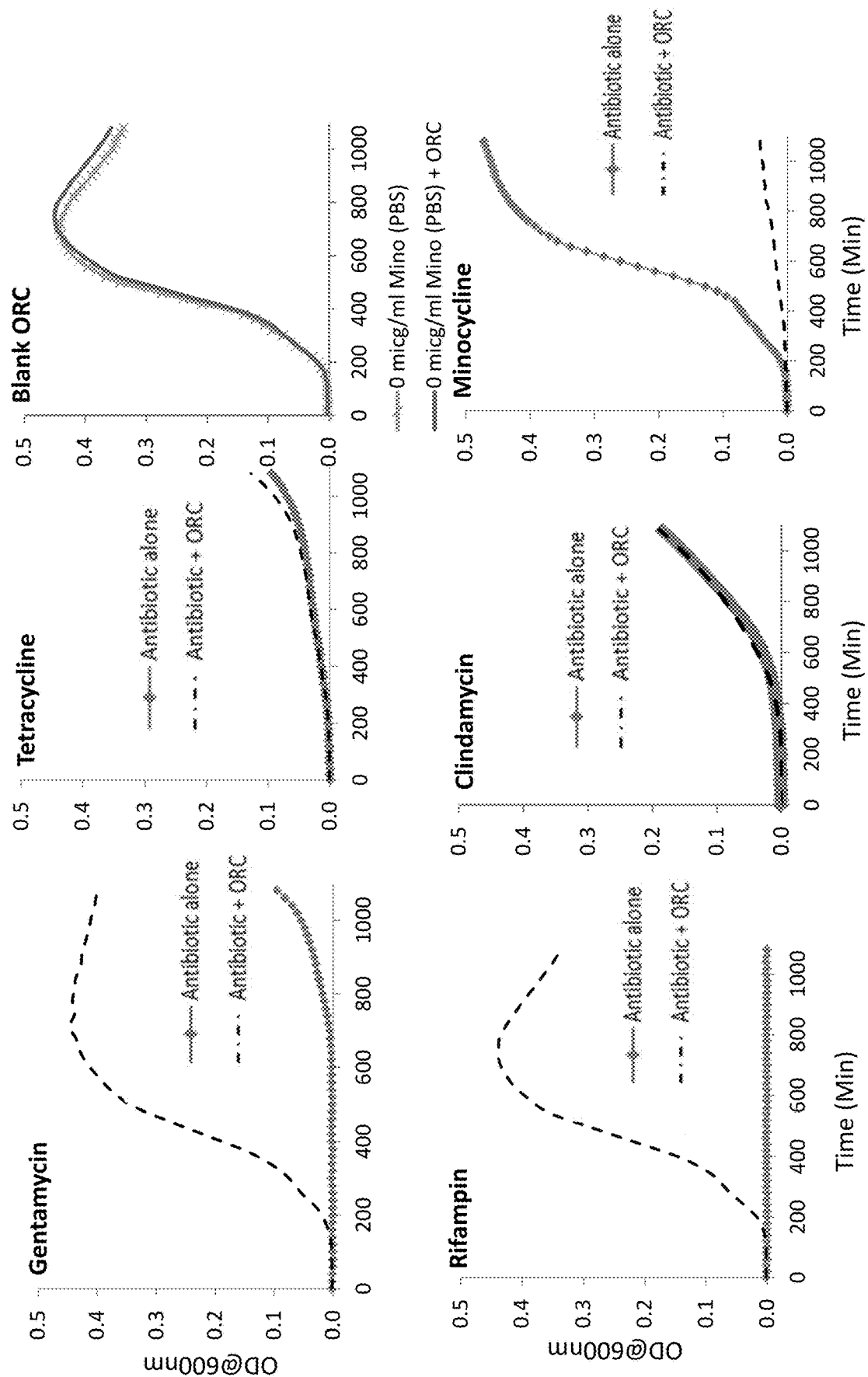

A summary of the results obtained for all the tested antibiotics is shown in FIG. 6. As shown in the upper and lower panels of the left side of FIG. 6, the increase in OD after treatment with gentamycin and ORC or rifampin and ORC, respectively, was greater than that obtained after treatment with the antibiotic alone, indicating that interference occurred between the antibiotic and ORC in each case and said interference resulting in lowering the antibiotic activity.

As shown in the upper and lower panels of the middle of FIG. 6, the increase in OD after treatment with clindamycin and ORC, or tetracycline and ORC, respectively, was substantially the same as that obtained after treatment with the antibiotic alone, indicating that no interference occurred between clindamycin and ORC or tetracycline and ORC.

As shown in the upper panel at the right of FIG. 6, the increase in OD after no minocycline treatment was substantially the same as that obtained with ORC alone.

As shown in FIG. 6, the decrease in OD after treatment with minocycline together with ORC was significantly greater than that obtained after treatment with either ORC (the upper panel in the right of the figure) or the antibiotic alone, indicating that a synergistic effect occurred between minocycline and ORC.

Example 3: Tertiary Stage Determination of Antimicrobial Activity of Orc Pads Impregnated with a Single or Combination Antibiotic This stage comprised testing the antimicrobial activity of antibiotic-impregnated ORC pads in order to identify a suitable concentration range for single or multiple antibiotics in the antibiotic-impregnated ORC pads for use in prevention of SSI.

a. Determination of Antibiotic Impregnation Levels

In order to determine the quantity of antibiotic impregnated into an ORC pad, the antibiotic was extracted out of the pad and the antibiotic levels were measured.

Impregnation was carried out as described above in section "Preparation of antibiotic impregnated ORC extracts" under "Methods". Briefly, ORC patches weighing on average 70 mg each were impregnated with the selected antibiotic.

Samples of pads impregnated with rifampin, minocycline and clindamycin, as well as blank ORC pads (w/o impregnated antibiotics) were taken for antibiotic loading analysis.

Each sample was weighed and placed in a 15 ml scintillation vial and 1 ml of methanol was added.

The vials were hand shaken periodically and after 2 hours the methanol was decanted off for analysis ("$1^{st}$ extract"). A second 1 ml of methanol was added into the scintillation vial, and the process was repeated to obtain the "$2^{nd}$ extract".

A third 1 ml of methanol was added into the scintillation vial, and the process was repeated to obtain the "$3^{rd}$ extract".

The 1' extract, $2^{nd}$ extract, and the $3^{rd}$ extract were then analyzed by LC/UV/MS using an Agilent 1260 Series UPLC with photodiode array detector and Agilent 1100 MSD mass spectrometer.

The concentration of the antibiotic in each extract was estimated by using the calibration curve of corresponding standards (peak area at 350 nm for rifampicin; 425 and 458 peak area for clindamycin and minocycline, respectively).

Results are presented in Table 9 below.

TABLE 9

| | Impregnation Loading Solution | Antibiotic Conc. per ORC pad (µg/g) | | | Total Antibiotic impregnation |
|---|---|---|---|---|---|
| Antibiotic | Conc. (µg/ml) | $1^{st}$ extract | $2^{nd}$ extract | $3^{rd}$ extract | level in ORC pad (µg/g) |
| Minocycline | 20 | 8.9 | 1.9 | <1.4 | 10.8 |
| Clindamycin | 10 | 10.7 | 2.1 | <1.4 | 12.8 |
| Rifampin | 200 | 409.2 | 139.0 | 79.9 | 628.2 |

The results presented in Table 9 were then used to calculate the amount of antibiotic loaded on the rest of the antibiotic-impregnated ORC patches used in the present studies. As a linear dilution of the antibiotic was used in order to prepare the loading solution, a simple linear equation can be assigned in turn in order to deduct the level of antibiotic loaded onto the rest of the antibiotic impregnated patches.

ORC pads were impregnated with a single antibiotic or with a combination of two antibiotics. The antibiotic loading onto each of the patches tested, calculated according to the loading levels described in Table 9, are depicted in Table 10 below.

Table 10 shows ORC impregnation levels deduced according to the impregnation levels found in Table 9 above and their consequent concentrations in the following MIC experiments (see section b).

TABLE 10

| | Impregnation Loading Solution Conc. (μg/ml) | Total antibiotic impregnation level in ORC pad (μg/g) | Total Antibiotic impregnation level in ORC pad (%) | Antibiotic concentration in MIC experiment (ng/ml) |
|---|---|---|---|---|
| Rifampin | 200 | 628.2 | 0.06282 | 1465.8 |
| | 150 | 471.15 | 0.047115 | 1099.35 |
| | 100 | 314.1 | 0.03141 | 732.9 |
| | 50 | 157.05 | 0.015705 | 366.45 |
| | 40 | 125.64 | 0.012564 | 293.16 |
| | 30 | 94.23 | 0.009423 | 219.87 |
| | 20 | 62.82 | 0.006282 | 146.58 |
| | 10 | 31.41 | 0.003141 | 73.29 |
| Clindamycin | 20 | 25.6 | 0.00256 | 59.73 |
| | 10 | 12.8 | 0.00128 | 29.87 |
| | 5 | 6.4 | 0.00064 | 14.93 |
| | 2.5 | 3.2 | 0.00032 | 7.47 |
| | 3 | 3.84 | 0.000384 | 8.96 |
| | 2 | 2.56 | 0.000256 | 5.97 |
| | 1.5 | 1.92 | 0.000192 | 4.48 |
| | 1 | 1.28 | 0.000128 | 2.98 |
| | 0.5 | 0.64 | 0.000064 | 1.49 |
| Minocycline | 40 | 21.6 | 0.00216 | 50.4 |
| | 20 | 10.8 | 0.00108 | 25.2 |
| | 10 | 5.4 | 0.00054 | 12.6 |
| | 5 | 2.7 | 0.00027 | 6.3 |
| | 4 | 2.16 | 0.000216 | 5.04 |
| | 3 | 1.62 | 0.000162 | 3.78 |
| | 2 | 1.08 | 0.000108 | 2.52 |
| | 1 | 0.54 | 0.000054 | 1.26 | b. Antimicrobial Activity of ORC Pads Impregnated with Different Concentrations of a Single Antibiotic ORC pads impregnated with a single antibiotic were tested for antimicrobial activity using the MIC measurement described in Example 2 above. Briefly, ORC patches weighing on average 70 mg each were impregnated with the selected antibiotic. Antibiotic-impregnated ORC extracts were prepared by immersion and incubation in 3 ml of sterile PBS for 3 hours at ambient temperature. The ORC was then removed and any remaining ORC particles were filtered out using a 0.8/0.4 μm syringe filter. This extraction fluid was then diluted 10-fold into Muller Hinton growth medium containing bacteria. Bacterial growth was monitored every 20 min for a total of 18 hours according to optical density (OD) at 600 nm, using an ELISA reader.

Tables 11a summarizes the results obtained used single antibiotic-impregnated ORC pads according to their ET50 as described in Example 2. The results resemble those of the secondary stage MIC—see Example 2, and the synergistic effect of minocycline is even more pronounced when the antibiotic is impregnated onto the ORC.

TABLE 11a

| | Antibiotic conc. in impregnation fluid | μg/antibiotic per gr ORC | conc. in MIC ng/ml | ET50 |
|---|---|---|---|---|
| Minocycline | 40 μg/ml | 21.6 | 50.40 | >2000 |
| | 20 μg/ml | 10.8 | 25.20 | >2000 |
| | 10 μg/ml | 5.4 | 12.60 | 2000 |
| | 5 μg/ml | 2.7 | 6.30 | 1145 |
| | 0 μg/ml | 0 | 0 | 819.4 |
| Rifampin | 200 μg/ml | 628.2 | 1465.8 | >2000 |
| | 150 μg/ml | 471.15 | 1099.35 | >2000 |
| | 100 μg/ml | 314.1 | 732.9 | 1396 |
| | 50 μg/ml | 157.05 | 366.45 | 643 |
| | 0 μg/ml | 0 | 0 | 712.5 |

TABLE 11a-continued

| | Antibiotic conc. in impregnation fluid | μg/antibiotic per gr ORC | conc. in MIC ng/ml | ET50 |
|---|---|---|---|---|
| Clindamycin | 20 μg/ml | 25.6 | 59.73 | >2000 |
| | 10 μg/ml | 12.8 | 29.87 | >2000 |
| | 5 μg/ml | 6.4 | 14.93 | 1425 |
| | 2.5 μg/ml | 3.2 | 7.47 | 975.9 |
| | 0 μg/ml | 0 | 0 | 663.2 |

The MIC result presented in Table 11b below shows the reduction in the minocycline levels required in order to achieve antimicrobial activity. It is apparent that the ORC interference with Rifampin activity remains generating an MIC which was 50 times higher than that of the primary stage MIC. The MIC of Clindamycin was four times lower in the ORC from the impregnated ORC. However, the MIC of Minocycline was 20 times lower than that of the $1^{st}$ stage MIC further establishing the synergistic effect of minocycline and ORC.

The results showed that the impregnation process did not impair the synergism of minocycline and ORC described above, and that rifampin, the activity of which was detected as impaired, was also impaired once impregnated onto the ORC. These TABLE 11b

| Antibiotic | In-house (primary) MIC (μg/ml) | Antibiotic-impregnated ORC (tertiary) MIC (μg/ml) | Fold reduction in MIC concentration |
|---|---|---|---|
| Minocycline | 0.25 | 0.0126 | 19.85 |
| Rifampin | 0.015 | 0.733 | 0.019 |
| Clindamycin | 0.062 | 0.015 | 4.15 | c. Antimicrobial Activity of ORC Pads Impregnated with Different Concentrations of a Combination of Two Antibiotics Since a synergistic effect was observed between ORC and minocycline, minocycline was used in all combination studies. Combinations of: 1-minocycline and clindamycin; or 2-minocycline and rifampin were studied, as shown in Table 12 below.

TABLE 12

| μg Minocycline per gr ORC | μg Rifampin per gr ORC | Total | Result |
|---|---|---|---|
| 0.00 | 0.00 | 0.00 | 409 |
| 0.54 | 0.00 | 0.54 | 585.4 |
| 1.08 | 0.00 | 1.08 | 799.9 |
| 2.16 | 0.00 | 2.16 | >2000 |
| 2.70 | 0.00 | 2.70 | >2000 |
| 0.00 | 31.41 | 31.41 | 406.8 |
| 0.54 | 31.41 | 31.95 | 606.8 |
| 2.70 | 31.41 | 34.11 | 1264 |
| 0.00 | 62.82 | 62.82 | 442.3 |
| 1.08 | 62.82 | 63.90 | 881.2 |
| 2.16 | 62.82 | 64.98 | 1992 |
| 0.00 | 125.64 | 125.64 | 450.4 |
| 1.08 | 125.64 | 126.72 | 1482 |
| 2.16 | 125.64 | 127.80 | >2000 |
| 0.00 | 157.05 | 157.05 | 418.1 |
| 0.54 | 157.05 | 157.59 | >2000 |
| 2.70 | 157.05 | 159.75 | >2000 |

TABLE 12-continued

| µg Minocycline per gr ORC | µg Clindamycin per gr ORC | Total | Result |
|---|---|---|---|
| 0.00 | 0.00 | 0.00 | 434.8 |
| 0.54 | 0.00 | 0.54 | 637.6 |
| 1.08 | 0.00 | 1.08 | 1072 |
| 2.16 | 0.00 | 2.16 | >2000 |
| 2.70 | 0.00 | 2.70 | >2000 |
| 0.00 | 0.64 | 0.64 | 448.7 |
| 0.54 | 0.64 | 1.18 | 734.5 |
| 2.70 | 0.64 | 3.34 | >2000 |
| 0.00 | 1.28 | 1.28 | 485.1 |
| 1.08 | 1.28 | 2.36 | 1227 |
| 2.16 | 1.28 | 3.44 | >2000 |
| 0.00 | 2.56 | 2.56 | 521.1 |
| 1.08 | 2.56 | 3.64 | 1488 |
| 2.16 | 2.56 | 4.72 | >2000 |
| 0.00 | 3.84 | 3.84 | 579.8 |
| 0.54 | 3.84 | 4.38 | 1650 |
| 2.70 | 3.84 | 6.54 | >2000 |

Since the study included many possible combinations of two antibiotics, each with their own different concentration range, a matrix of possible antibiotic concentrations was designed, and ORC pads prepared accordingly (see Table 10). Since all the possible combinations could not be fitted into one 96 well plate, a series of MIC experiments were carried out. In order to compare between the different plates and obtain results which can provide information regarding the activity of the all antibiotics and concentrations tested, ET50 values (as described in Example 2) were used, which provided a quantitative measurement of the antibiotic activity which could be used to compare results from different assay plates.

Table 12 presents ET50 results for combinations of minocycline with rifampin or minocycline with clindamycin at different concentrations. The results show that 0.54 µg/gr minocycline in combination with 157.05 µg/gr rifampin (total 157.59 µg/gr antibiotic loaded), as well as 0.54 µg/gr minocycline in combination with 3.84 µg/gr clindamycin (total 4.38 µg/gr antibiotic loaded) is a sufficient level of antibiotics which provides a great antibiotic activity. In addition, a combination of 1.08 µg/gr minocycline with 125.64 µg/gr rifampin as well as 1.08 µg/gr minocycline with 2.56 µg/gr of clindamycin also provided a high level of antibiotic activity.

The primary stage study confirmed that no false positive antibacterial activity occurred, that the baseline antibacterial activity of the reagents and bacterial strains used was correct. The MIC obtained for *S. aureus* using a specific antibiotic alone was found to be consistent with values published in known literature.

In the secondary stage, it was shown that although it is reported that ORC itself has some intrinsic antimicrobial activity (Dineen P. "The effect of oxidized regenerated cellulose on experimental infected splenotomies" Journal of Surgical Research 1977; 23: 114-116); the amount of ORC used in the present study was ineffective in providing bacterial growth inhibition as determined by MIC studies. The selected antibiotics were shown to exhibit different activity levels in the presence of ORC. Specifically, rifampin and gentamycin activity was impaired by ORC and MIC was increased; clindamycin and tetracycline activity showed no change in the presence of ORC and no change in MIC. However, surprisingly, only minocycline MIC was reduced when mixed with ORC.

In the tertiary stage, ORC patches were impregnated with selected antibiotics including minocycline, rifampin and/or clindamycin. MIC results were found to be consistent with those of the secondary stage.

The levels of clindamycin required to be impregnated onto the ORC pad in order to achieve an inhibition of growth were similar to those of the first stage MIC, i.e. there was no change of clindamycin antimicrobial activity. The levels of rifampin required to be impregnated onto the ORC pad in order to achieve an inhibition of growth were about 50 times higher than those of the first stage MIC i.e. the rifampin activity was impaired even when impregnated onto the ORC pad. Finally, the levels of minocycline required to be impregnated onto the ORC pad in order to achieve an inhibitory effect were about 20 times lower than those of the first stage MIC.

It was further found that when minocycline is impregnated onto an ORC pad in combination with an additional antibiotic, the ET50 is reduced for both minocycline and the additional antibiotic, i.e. either rifampin or clindamycin. As little as 1.26 ng/ml minocycline together with 366.5 ng/ml rifampin or 8.9 ng/ml clindamycin were found to be sufficient for growth inhibition of *S. aureus*. The MIC for these antibiotics when used as single antibiotics in the absence of ORC (first stage MIC results) was found to be 250 ng/ml for minocycline, 62 ng/ml for clindamycin and 15 ng/ml for rifampin. These results prove a 200-fold reduction of the MIC for minocycline, and 6.8 fold reduction for clindamycin. Although the MIC for rifampin was higher than that seen as a single antibiotic, it remained less than that of the second stage MIC. Interestingly, even though minocycline is an antibiotic from the tetracycline family of antibiotics, the activity enhancement was restricted to minocycline and was not demonstrated for other members of the family (tetracycline).

The results demonstrate a synergistic effect for minocycline and ORC. A hemostatic ORC pad impregnated with a low concentration of minocycline will therefore be able to provide a high level of antibiotic activity. The recommended antibiotic concentration for minocycline alone in an ORC pad is in the range of from 2.7 to 21.6 µg per gram ORC. When minocycline is used in combination with rifampin or clindamycin, the recommended antibiotic concentrations are from 0.5 to 2.7 µg minocycline per gram ORC together with from 31.4 to 157 µg rifampin per gram ORC or from 0.6 to 3.8 µg clindamycin per gram ORC.

Example 4: Rat Wound Model of Antimicrobial Activity of ORC Pads Impregnated with Single or Combination Antibiotics This stage comprises testing the antimicrobial activity of antibiotic-impregnated ORC pads in vivo on full-thickness 1 cm² skin wounds, in order to assess the effectiveness of such pads for the treatment of SSI. The wound area is contaminated, treated, excised and then bacterial load on the wound area is quantitatively assessed after being cultured 24 hours later.

Young female specific pathogen-free Sprague-Dawley rats are kept in standard housing with food and water ad libitum and 12-hour light/dark cycles.

Materials to be used are as described for in vitro studies above.

Antibiotics to be used in the tests are rifampin, tetracycline, minocycline and clindamycin.

Solutions comprising each of the antibiotics to be tested, both as single antibiotics and in combinations of two or three antibiotics, are prepared in methanol.

Blank ORC pads of dimensions 1×1.5 inch, weighing between 65-75 mg (70 mg on average), in duplicate, are immersed in the antibiotic solutions as described above for Example 3, and then dried using a rotary evaporator to provide antibiotic-impregnated ORC pads. As controls pads blank ORC pads immersed in methanol alone are prepared. As additional control, solutions of the single or combination antibiotics alone (i.e. without use of ORC pads) are used.

Rats are anesthetized with oxygen with 1% isoflurane and hair from the skin overlying the dorsal cervical spine and interscapular region is removed with an electric razor. A 1×1.5 inch full-thickness piece of skin is excised. A bacterial inoculum of $2.5 \times 10^8$ CFU suspended in 250 µl of sterile saline is injected into the loose subcutaneous connective tissue.

Antibiotic-impregnated ORC pads, antibiotics alone (as for MIC testing described in Example 3, Table 11a) or blank ORC test pads as control are applied to the surface of the wound.

A sterile piece of non-adherent dressing is affixed to the wound. Animals are recovered from anaesthesia and returned to standard housing.

After 24 hours, animals are euthanized under anaesthesia and the sterile dressing removed from the wound. The entirety of the contaminated subcutaneous tissue, including any adherent ORC pad, is debrided down to, but not including the intercapsular paraspinous muscles. The excised material is homogenized and used for quantitative culture.

Comparison of wound bacterial burden between animals treated with antibiotic-impregnated ORC pads and with ORC pads alone as control are performed.

It is found that ORC pads impregnated with minocycline are more effective in preventing wound contamination such as SSI than either ORC pads alone or solutions of minocycline in PBS.

In addition, it is found that ORC pads impregnated with a combination of minocycline with an additional antibiotic, such as minocycline and rifampin or minocycline and clindamycin, are more effective in preventing wound contamination than either ORC pads alone or ORC pads impregnated with either rifampin or clindamycin, without minocycline, or than solutions of the same combination of antibiotics in PBS, without the use of ORC pads.

The in vivo results demonstrate a synergistic effect for minocycline and ORC or minocycline and ORC combined with rifampin or clindamycin.

The invention claimed is:

1. An antimicrobial composition comprising an absorbable oxidized regenerated cellulose (ORC) pad and an antibiotic being minocycline, wherein the minocycline is dispersed or impregnated on and/or within the ORC pad and is present at an effective concentration of from about 0.013 µg to about 0.105 µg per $cm^2$ of ORC pad, wherein the carboxyl content of the ORC is about 12% to about 21%, by weight.

2. The antimicrobial composition of claim 1, being devoid of an additional antibiotic.

3. An antimicrobial composition comprising an absorbable oxidized regenerated cellulose (ORC) pad, an antibiotic being minocycline, and at least one additional antibiotic, wherein the minocycline is dispersed or impregnated on and/or within the ORC pad and is present at an effective concentration of from about 0.0024 µg to about 0.013 µg per $cm^2$ of ORC pad, wherein the carboxyl content of the ORC is about 12% to about 21%, by weight.

4. The antimicrobial composition of claim 3, wherein said at least one additional antibiotic is selected from the group consisting of rifampin, clindamycin and a combination thereof.

5. The antimicrobial composition of claim 3, wherein the at least one additional antibiotic comprises rifampin at a concentration of from about 31.4 µg to about 157 µg per 1.0 g of ORC.

6. The antimicrobial composition of claim 3, wherein the at least one additional antibiotic comprises clindamycin at a concentration of from about 0.6 µg to about 3.8 µg per 1.0 g of ORC.

7. A kit comprising the absorbable ORC pad with minocycline according to claim 1.

* * * * *